(12) United States Patent
Liu

(10) Patent No.: US 10,936,052 B2
(45) Date of Patent: Mar. 2, 2021

(54) METHOD AND DEVICE FOR DETERMINING HEAD MOVEMENT ACCORDING TO ELECTROOCULOGRAPHIC INFORMATION

(71) Applicant: Beijing Zhigu Rui Tuo Tech Co., Ltd, Beijing (CN)

(72) Inventor: Hao Liu, Beijing (CN)

(73) Assignee: BEIJING ZHIGU RUI TUO TECH CO., LTD, Beijing (CN)

(*) Notice: Subject to any disclaimer, the term of this patent is extended or adjusted under 35 U.S.C. 154(b) by 686 days.

(21) Appl. No.: 15/567,954

(22) PCT Filed: Apr. 20, 2016

(86) PCT No.: PCT/CN2016/079744
§ 371 (c)(1),
(2) Date: Oct. 19, 2017

(87) PCT Pub. No.: WO2016/169476
PCT Pub. Date: Oct. 27, 2016

(65) Prior Publication Data
US 2018/0144191 A1    May 24, 2018

(30) Foreign Application Priority Data
Apr. 20, 2015 (CN) .......................... 201510185762.8

(51) Int. Cl.
| | | |
|---|---|---|
| G06F 3/01 | (2006.01) | |
| A61B 5/00 | (2006.01) | |
| A61B 3/113 | (2006.01) | |
| A61B 5/0496 | (2006.01) | |
| A61B 5/11 | (2006.01) | |
| G06F 17/15 | (2006.01) | |
| G06K 9/00 | (2006.01) | |
| G02B 27/01 | (2006.01) | |

(52) U.S. Cl.
CPC ............ *G06F 3/012* (2013.01); *A61B 3/113* (2013.01); *A61B 5/0496* (2013.01);
(Continued)

(58) Field of Classification Search
CPC .......... G06F 3/012; G06F 3/015; G06F 3/017; G06F 17/15; A61B 5/0488; A61B 5/0496;
(Continued)

(56) References Cited

U.S. PATENT DOCUMENTS

| | | | |
|---|---|---|---|
| 5,726,916 A | 3/1998 | Smyth | |
| 8,121,694 B2* | 2/2012 | Molnar | ............ A61B 5/04014 607/45 |

(Continued)

FOREIGN PATENT DOCUMENTS

| | | |
|---|---|---|
| CN | 1767873 A | 5/2006 |
| CN | 101308400 A | 11/2008 |

(Continued)

OTHER PUBLICATIONS

Machine Translation of KR-100310036-B1 (published Sep. 12, 2001) created on Jun. 9, 2020. (Year: 2001).*

(Continued)

*Primary Examiner* — Nicholas Ulrich
(74) *Attorney, Agent, or Firm* — Amin, Turocy & Watson, LLP

(57) ABSTRACT

Methods and devices for determining a head movement are provided. A method comprises: acquiring, in response to a head movement performed by a user, a piece of electrooculographic information of the user; and determining information related to the head movement according to the piece of electrooculographic information and at least one piece of reference information. The head movement can be identified according to electrooculographic information. For some devices integrated with electrooculographic sensors, the electrooculographic sensor can be reused to collect the electrooculographic information, and thereby reduce implementation costs.

22 Claims, 5 Drawing Sheets

S120
Acquire, in response to a head movement performed by a user, a piece of electrooculographic information of the user S140
Determine information related to the head movement according to the piece of electrooculographic information and at least one piece of reference information

(52) U.S. Cl.
CPC .......... *A61B 5/1123* (2013.01); *A61B 5/6814* (2013.01); *G06F 3/013* (2013.01); *G06F 17/15* (2013.01); *G06K 9/0053* (2013.01); *G06K 9/00335* (2013.01); *G06K 9/00536* (2013.01); *G06K 9/00604* (2013.01); *A61B 5/6803* (2013.01); *G02B 2027/0178* (2013.01); *G02B 2027/0187* (2013.01)

(58) Field of Classification Search
CPC ............... A61B 5/1123; G06K 9/0053; G06K 9/00496; G06K 9/00523; G06K 9/00536; G06K 9/00543; G06K 9/0055; G06K 9/00557; G02B 2027/0187
See application file for complete search history.

(56) References Cited

U.S. PATENT DOCUMENTS

| | | | |
|---|---|---|---|
| 2003/0046254 A1* | 3/2003 | Ryu | A61F 4/00 706/15 |
| 2005/0268916 A1 | 12/2005 | Mumford et al. | |
| 2014/0369537 A1 | 12/2014 | Pontoppidan et al. | |

FOREIGN PATENT DOCUMENTS

| | | | |
|---|---|---|---|
| CN | 102968072 A | 3/2013 | |
| CN | 103211594 A | 7/2013 | |
| CN | 103336580 A | 10/2013 | |
| CN | 104503592 A | 4/2015 | |
| CN | 104503593 A | 4/2015 | |
| KR | 100310036 B1 * | 9/2001 | |
| WO | WO-2004021157 A1 * | 3/2004 | ............. G06F 3/015 |
| WO | 2016115982 A1 | 7/2016 | |

OTHER PUBLICATIONS

Chinese Office Action dated Oct. 31, 2018 for Chinese Patent Application No. 201510185762.8, 23 pages (with translation).
International Search Report for PCT Application No. PCT/CN2016/079744, dated Jul. 15, 2016, 3 pages.
Zhang Xu, et al., "Exploration on the Feasibility of Building Muscle-Computer Interfaces using Neck and Shoulder Motions", 31st Annual International Conference of the IEEE EMBS, Minneapolis, Minnesota, USA, Sep. 2-6, 2009, 4 pages.

* cited by examiner

METHOD AND DEVICE FOR DETERMINING HEAD MOVEMENT ACCORDING TO ELECTROOCULOGRAPHIC INFORMATION

RELATED APPLICATION

The present application is a U.S. National Stage filing under 35 U.S.C. § 371 of international patent cooperation treaty (PCT) application No. PCT/CN2016/079744, filed Apr. 20, 2016, and entitled "METHOD AND DEVICE FOR DETERMINING HEAD MOVEMENT", which claims the benefit of priority to Chinese Patent Application No. 201510185762.8, filed on Apr. 20, 2015, which applications are hereby incorporated into the present application by reference herein in their respective entireties.

TECHNICAL FIELD

The present application relates to the field of electronic devices, and, for example, to a method and device for determining a head movement.

BACKGROUND

Currently, new technologies such as wearable computing, mobile computing, and pervasive computing develop rapidly, which put forward new challenges and higher requirements for human computer interaction technology and provide many new opportunities. In this phase, the nature and harmony of human computer interaction manner gets a certain development, and the main characteristic thereof is an multi-channel interaction based on input means such as postures, voice, handwriting, tracking, and expressions, and the objective thereof is to make people perform an interaction operation in a nature way such as using an action, voice, and an expression, which is "user freedom" emphasized by ideal human computer interaction.

In the traditional method for identifying a head movement, a speed sensor, a gyroscope, or the like is generally disposed on a head, and then a corresponding head movement is identified according to information such as a speed change and an angle change generated during the head movement.

The foregoing method for identifying a head movement requires a hardware device such as a speed sensor, which increases implementation costs.

SUMMARY

An example objective of the present application is to provide a method and device for determining a head movement, so as to reduce implementation costs.

According to one aspect of at least one example embodiment of the present application, a method for determining a head movement is provided. The method comprises:

acquiring, in response to a head movement performed by a user, a piece of electrooculographic information of the user; and determining information related to the head movement according to the piece of electrooculographic information and at least one piece of reference information.

According to one aspect of at least one example embodiment of the present application, a device for determining a head movement is provided. The device comprises:

an acquiring module, configured to acquire, in response to a head movement performed by a user, a piece of electrooculographic information of the user; and a determining module, configured to determine information related to the head movement according to the piece of electrooculographic information and at least one piece of reference information.

In example embodiments of the present application, in response to a head movement performed by a user, a piece of electrooculographic information of the user is acquired, and according to the piece of electrooculographic information and at least one piece of reference information, information related to the head movement is determined. Therefore, a method for identifying a head movement according to electrooculographic information is provided. For some devices integrated with electrooculographic sensors, such as pairs of smart glasses, the method may be used to reuse the electrooculographic sensor to collect the electrooculographic information, and thereby reducing implementation costs.

DETAILED DESCRIPTION

Example embodiments of the present application are further described in detail below with reference to the accompanying drawings and embodiments. The following embodiments are intended to describe the present application, but not to limit the scope of the present application.

A person skilled in the art understands that, in embodiments of the present application, the value of the serial number of each step does not mean an execution sequence, and the execution sequence of each step should be determined according to the function and internal logic thereof, and should not be any limitation to the implementation procedure of embodiments of the present application.

Figure 1:
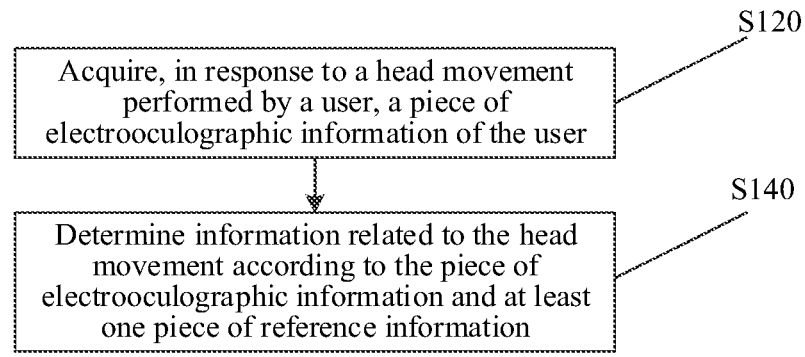
FIG. 1 is a flowchart of a method for determining a head movement according to an example embodiment of the present application.

FIG. 1 is a flowchart of a method for determining a head movement according to an embodiment of the present application. The method may be implemented, for example, on a device for determining a head movement. As shown in FIG. 1, the method comprises:

S120: acquire, in response to a head movement performed by a user, a piece of electrooculographic information of the user; and S140: determine information related to the head movement according to the piece of electrooculographic information and at least one piece of reference information.

In the method according to an example embodiment of the present application, in response to a head movement performed by a user, a piece of electrooculographic information of the user is acquired, and according to the piece of electrooculographic information and at least one piece of reference information, information related to the head movement is determined. Therefore, a method for identifying a head movement according to electrooculographic information is provided. For some devices integrated with electrooculographic sensors, such as pairs of smart glasses, the method may be used to reuse the electrooculographic sensor to collect the electrooculographic information, and thereby reducing implementation costs.

The following describes functions of the steps S120 and S140 in detail with reference to the example embodiments.

S120: Acquire, in response to a head movement performed by a user, a piece of electrooculographic information of the user.

The head movement refers to a movement performed by the head of the user, for example, head nodding and head shaking. The electrooculographic information may be electrooculographic information of the left eye or electrooculographic information of the right eye of the user, and for example, the electrooculographic information may be acquired by using an electrooculographic sensor on a pair of smart glasses.

S140: Determine information related to the head movement according to the piece of electrooculographic information and at least one piece of reference information.

The information related to the head movement may comprise type of the head movement, for example, head nodding and head shaking. Correspondingly, the step S140 may comprise:

S141: determine the type of the head movement according to the piece of electrooculographic information and the at least one piece of reference information.

In an example embodiment, the step S141 may comprise:

S1411a: determine a target waveform in the piece of electrooculographic information; and S1412a: determine the type of the head movement according to the target waveform and at least one reference waveform.

In the step S1411a, the target waveform is a waveform corresponding to the head movement in waveforms of the electrooculographic information, which is significantly different from waveforms of electrooculographic information collected when the head does not perform any movement.

Figure 2:
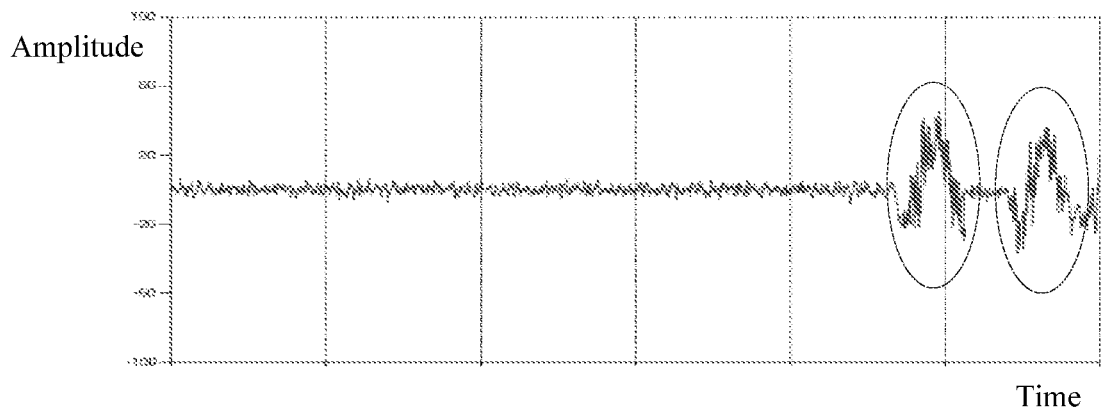
FIG. 2 is a schematic waveform diagram of electrooculographic information corresponding to a head nodding movement according to an example embodiment of the present application.

Using an example in which the type of the head movement is head nodding movement for example, the obtained waveforms of the electrooculographic information are shown in FIG. 2. Waveforms in ellipses are waveforms when the head of the user performs the head nodding movement, and waveforms outside the ellipses are waveforms when the head of the user does not perform any movement. It can be seen that in FIG. 2, the waveforms in the ellipses are significantly different from the waveforms outside the ellipses. Specifically, amplitudes of the waveforms in the ellipses are obviously larger than amplitudes of the waveforms outside the ellipses. Based on this, the target waveforms can be extracted from the electrooculographic information, that is, the waveforms in the ellipses are determined as the target waveforms.

Figure 3:
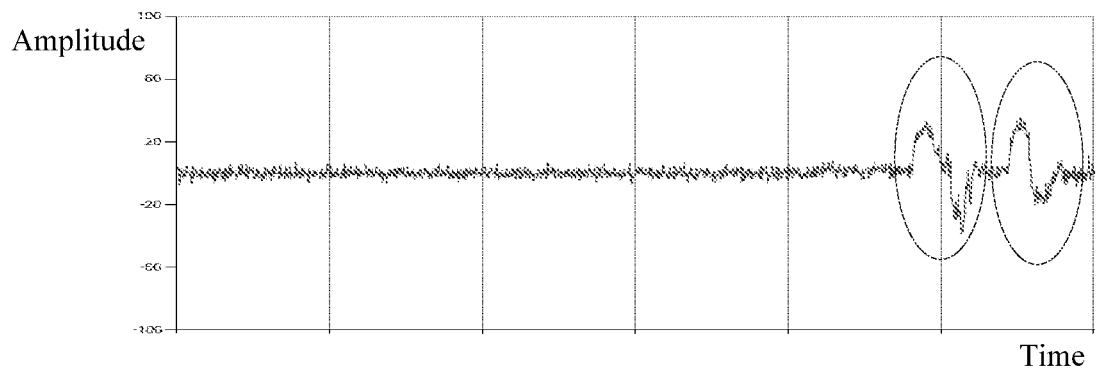
FIG. 3 is a schematic waveform diagram of electrooculographic information corresponding to a head shaking movement according to an example embodiment of the present application.

Similarity, FIG. 3 shows waveforms of the electrooculographic information obtained when the type of the head movement is head shaking. Waveforms in ellipses are waveforms when the head of the user performs the head shaking movement, and waveforms outside the ellipses are waveforms when the head of the user does not perform any movement. It can be seen that in FIG. 3, amplitudes of the waveforms in the ellipses are also obviously larger than amplitudes of the waveforms outside the ellipses. Based on this, it can be determined that the waveforms in the ellipses are the target waveforms.

In the step S1412a, the reference waveform may be a waveform that corresponds to a corresponding head movement obtained through pre-training, for example, during the training phase, the user may be trained to perform head movements of different types, and the corresponding waveforms are correspondingly acquired as the reference waveforms. For example, during the training phase, the user is trained to perform a head nodding movement, and a waveform in the ellipse in FIG. 2 is correspondingly acquired as a reference waveform corresponding to the head nodding movement.

When the number of the at least one reference waveform is relatively smaller, that is, when there are relatively fewer types of the head movements, whether the target waveform comprises the at least one reference waveform can be determined in an image recognition manner, and if yes, it is determined that the type of the head movement is a type corresponding to the comprised reference waveform. Taking FIG. 2 and FIG. 3 for example, it can be seen that the target waveforms in FIG. 2 are significantly different from the target waveforms in FIG. 3. For example, the trend of the target waveforms in FIG. 2 is first descending and then ascending, and the trend of the target waveforms in FIG. 3 is first ascending and then descending. Based on the foregoing difference, it can be determined that the target waveforms correspond to different reference waveforms, that is, the target waveforms are identified.

When the number of the at least one reference waveform is relatively large, a probability of confusing different reference waveforms is increasing. In order to avoid an identification error, in an example embodiment, the step S1412a may comprise:

S1412a': calculate cross correlations between the target waveform and the at least one reference waveform respectively, and determine the type of the head movement according to a calculation result.

Specifically, cross correlations between the target waveform and the at least one reference waveform respectively may be calculated to obtain calculation results corresponding to each reference waveform, and then the type corresponding to the reference waveform whose value of the calculation result is the highest (that is, reference waveform that has the highest degree of correlation with the target waveform) may be selected as the type of the head movement. For example, assume that the at least one reference waveform comprises a first reference waveform corresponding to head nodding and a second reference waveform corresponding to head shaking, a cross correlation between the first reference waveform and the target waveform is calculated to obtain a first result, and a cross correlation between the second reference waveform and the target waveform is calculated to obtain a second result, and if the value of the first result is higher than the value of the second result, it can be determined that the type of the head movement is head nodding.

In another example embodiment, the step S141 may comprise:

S1411b: determine a target signal characteristic in the piece of electrooculographic information; and S1412b: determine the type of the head movement according to the target signal characteristic and at least one reference signal characteristic.

In the step S1411b, the target signal characteristic may be understood as a signal characteristic of the target waveform in the foregoing example embodiment, which is correlated with at least one of an amplitude, a phase, and a spectrum of the target waveform. Specifically, the target signal characteristic may comprise at least one of a fingerprint, an average value, and a difference; the fingerprint may be composed of at least one of the amplitude, phase, and spectrum of the target waveform; the average value may be an average value of at least one of the amplitude, phase, and spectrum of the target waveform; and the difference may be a difference of at least one of the amplitude, phase, and spectrum of the target waveform. Certainly, a person skilled in the art understands that the target signal characteristic may be directly determined according to data of the electrooculographic information, and does not have to be determined according to the target waveform.

In the step S1412b, the reference signal characteristic may be a signal characteristic that corresponds to a corresponding head movement obtained through pre-training, for example, during the training phase, the user may be trained to perform head movements of different types and signal characteristics of the corresponding electrooculographic information are correspondingly acquired as the reference signal characteristics. For example, during the training phase, the user is trained to perform a head nodding movement, and a signal characteristic of the waveform in the ellipse in FIG. 2 is correspondingly acquired as a reference signal characteristic corresponding to the head nodding movement.

In the step S1412b, whether the target signal characteristic comprises the at least one reference signal characteristic can be determined in a signal characteristic comparison manner, and if yes, it is determined that the type of the head movement is a type corresponding to the comprised reference signal characteristic.

The type of the head movement may indicate different operating commands, for example, head nodding indicates confirmation and head shaking indicates cancelation. Meanwhile, for head movements of different types, different numbers of execution times may also indicate different operating commands, for example, a single head nodding indicates selected and two continuous head noddings indicate open. Therefore, in an example embodiment, the head movement comprises a first type head movement; and the at least one piece of reference information comprises first reference information corresponding to the first type head movement.

Correspondingly, the step S140 may further comprise:

S142: determine the number of times of the first type head movement according to the piece of electrooculographic information and the first reference information.

In an example embodiment, the step S142 may comprise:

S1421a: determine the target waveform in the piece of electrooculographic information; and S1422a: determine the number of times of the first type head movement according to the number of first reference waveforms comprised in the target waveform.

The implementation principle of the step S1421a is the same as that of the step S1411a, and no further details are provided herein again.

In the step S1422a, the number of the first reference waveforms comprised in the target waveform is corresponding to the number of times of the first type head movement. Assume that the first type head movement is head nodding, and the first reference waveform is a reference waveform corresponding to the head nodding. Taking FIG. 2 for example, it can be seen that the target waveform comprises two first reference waveforms, so that it can be determined that the user nods twice. Similarity, the electrooculographic information shown in FIG. 3 indicates that the user shakes the head twice.

In another example embodiment, the step S142 may comprise:

S1421b: determine the target signal characteristic in the piece of electrooculographic information; and S1422b: determine the number of times of the first type head movement according to the number of first reference signal characteristics comprised in the target signal characteristic.

A principle of the step S1421b can be the same as that of the step S1411b, and no further details are provided herein again.

In the step S1422b, the target signal characteristic comprises the number of the first reference signal characteristics, which is corresponding to the number of times of the first type head movement. Still assume that the first type head movement is head nodding, and assume that the first reference signal characteristic is amplitude changing data (for example, the amplitude is decreased to smaller than −20 first, and then increased to greater than 20, and decreased to smaller than −20 again) corresponding to the head nodding. Taking FIG. 2 for example, it can be seen that the target signal characteristic in the electrooculographic information comprises two first reference signal characteristics, so that it can be determined that the user nods twice. Certainly, a person skilled in the art understands that in the step, the waveform curve shown in FIG. 2 does not have to be obtained. Similarity, the electrooculographic information shown in FIG. 3 indicates that the user shakes the head twice.

In addition, the head movement may further comprise head movements of other types, for example, a second type head movement, or the head movement may comprise head movements of multiple types simultaneously, for example, the head movement may comprise the first type head movement and the second type head movement simultaneously, and identification of the number of times of the head movements of various types may be implemented according to the foregoing principle.

Figure 4:
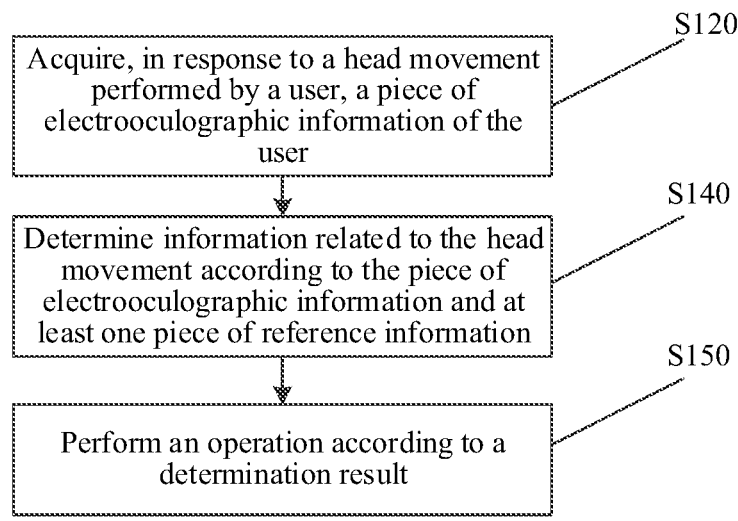
FIG. 4 is a flowchart of a method for determining a head movement according to an example embodiment manner of the present application.

Referring to FIG. 4, in an example embodiment, the method may further comprise:

S150: perform an operation according to a determination result.

The performed operation may comprise operations such as mode switching, content entering, user reminding, and device matching.

For example, during a process in which a user wears a pair of glasses, head movements of the user may be monitored, and if the user nods once, the current object is selected, for example, the current displayed application icon is selected; if the user nods twice continuously, the current object is open directly; and if the user shakes the head, a next object is switched to.

In addition, an embodiment of the present application further provides a computer readable medium, comprising computer readable instructions for performing the following operations when being executed: performing operations in the steps S120 and S140 in the method of the example embodiment shown in the foregoing FIG. 1.

In summary, in a method according to an embodiment of the present application, a head movement of a user may be determined according to electrooculographic information, and a corresponding operation is performed, which facilitates the user to control a corresponding electronic device by a head movement without adding implementation costs.

Figure 5:
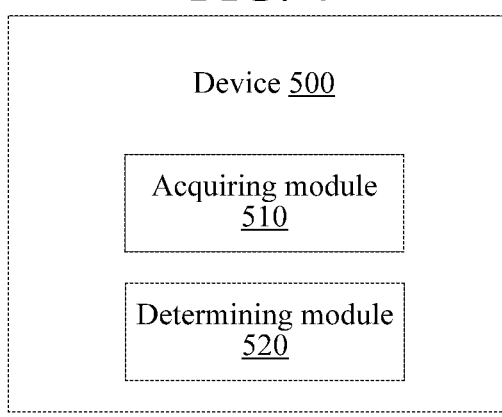
FIG. 5 is a module diagram of a device for determining a head movement according to another example embodiment of the present application.

FIG. 5 is a schematic module structural diagram of a device for determining a head movement according to an embodiment of the present application. The device may be an independent device for identifying a head movement, and certainly, the device may further be a functional module integrated in a wearable device such as a pair of glasses. Referring to FIG. 5, the device 500 may comprise:

an acquiring module 510, configured to acquire, in response to a head movement performed by a user, a piece of electrooculographic information of the user; and a determining module 520, configured to determine information related to the head movement according to the piece of electrooculographic information and at least one piece of reference information.

In a device according to an embodiment of the present application, in response to a head movement performed by a user, a piece of electrooculographic information of the user is acquired, and according to the piece of electrooculographic information and at least one piece of reference information, information related to the head movement is determined. Therefore, a method for identifying a head movement according to electrooculographic information is provided. For some devices integrated with electrooculographic sensors, such as pairs of smart glasses, the method may be used to reuse the electrooculographic sensor to collect the electrooculographic information, and thereby reducing implementation costs.

The following describes functions of the acquiring module 510 and the determining module 520 in detail with reference to the example embodiments.

The acquiring module 510 is configured to acquire, in response to a head movement performed by a user, a piece of electrooculographic information of the user.

The head movement refers to a movement performed by the head of the user, for example, head nodding and head shaking. The electrooculographic information may be electrooculographic information of the left eye or electrooculographic information of the right eye of the user, and for example, may be acquired by using an electrooculographic sensor.

The determining module 520 is configured to determine information related to the head movement according to the piece of electrooculographic information and at least one piece of reference information.

Figure 6:
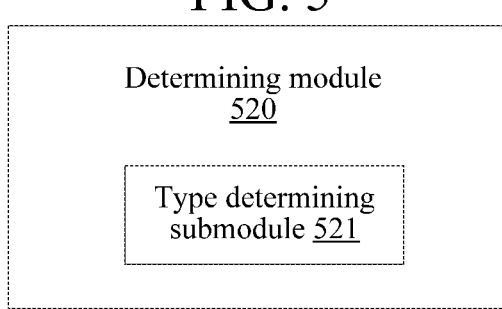
FIG. 6 is a module diagram of a determining module according to an example embodiment of the present application.

The information related to the head movement may comprise type of the head movement, for example, head nodding and head shaking. In an example embodiment, referring to FIG. 6, the determining module 520 comprises:

a type determining submodule 521, configured to determine the type of the head movement according to the piece of electrooculographic information and the at least one piece of reference information.

Figure 7:
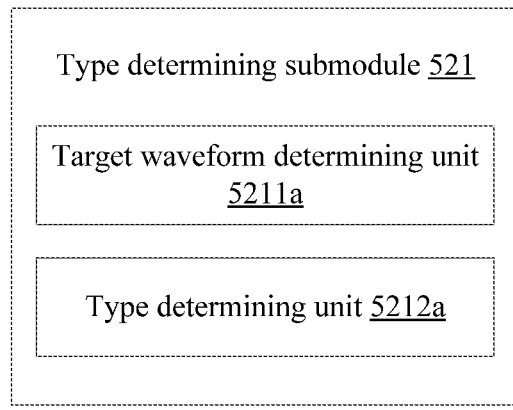
FIG. 7 is a module diagram of a type determining submodule according to an example embodiment of the present application.

In an example embodiment, referring to FIG. 7, the type determining submodule 521 may comprise:

a target waveform determining unit 5211a, configured to determine a target waveform in the piece of electrooculographic information; and a type determining unit 5212a, configured to determine the type of the head movement according to the target waveform and at least one reference waveform.

In the target waveform determining unit 5211a, the target waveform is a waveform corresponding to the head movement in waveforms of the electrooculographic information, which is significantly different from waveforms of electrooculographic information collected when the head does not perform any movement.

Using an example in which the type of the head movement is head nodding movement for example, the obtained waveforms of the electrooculographic information are shown in FIG. 2. Waveforms in ellipses are waveforms when the head of the user performs the head nodding movement, and waveforms outside the ellipses are waveforms when the head of the user does not perform any movement. It can be seen that in FIG. 2, the waveforms in the ellipses are significantly different from the waveforms outside the ellipses. Specifically, amplitudes of the waveforms in the ellipses are obviously larger than amplitudes of the waveforms outside the ellipses. Based on this, the target waveforms can be extracted from the electrooculographic information, that is, the waveforms in the ellipses are determined as the target waveforms.

Similarity, FIG. 3 shows waveforms of the electrooculographic information obtained when the type of the head movement is head shaking. Waveforms in ellipses are waveforms when the head of the user performs the head shaking movement, and waveforms outside the ellipses are waveforms when the head of the user does not perform any movement. It can be seen that in FIG. 3, amplitudes of the waveforms in the ellipses are also obviously larger than amplitudes of the waveforms outside the ellipses. Based on this, it can be determined that the waveforms in the ellipses are the target waveforms.

In the type determining unit 5212a, the reference waveform may be a waveform that corresponds to a corresponding head movement obtained through pre-training, for example, during the training phase, the user may be trained to perform head movements of different types and the corresponding waveforms are correspondingly acquired as the reference waveforms. For example, during the training phase, the user is trained to perform a head nodding movement, and a waveform in the ellipse in FIG. 2 is correspondingly acquired as a reference waveform corresponding to the head nodding movement.

When the number of the at least one reference waveform is relatively smaller, that is, when there are relatively fewer types of the head movements, whether the target waveform comprises the at least one reference waveform can be determined in an image recognition manner, and if yes, it is determined that the type of the head movement is a type corresponding to the comprised reference waveform. Taking FIG. 2 and FIG. 3 for example, it can be seen that the target waveforms in FIG. 2 are significantly different from the target waveforms in FIG. 3. For example, the trend of the target waveforms in FIG. 2 is first descending and then ascending, and the trend of the target waveforms in FIG. 3 is first ascending and then descending. Based on the foregoing difference, it can be determined that the target waveforms correspond to different reference waveforms, that is, the target waveforms are identified.

When the number of the at least one reference waveform is relatively large, a probability of confusing different reference waveforms is increasing. In order to avoid an identification error, in an example embodiment, the type determining unit 5212a is configured to calculate cross correlations between the target waveform and the at least one reference waveform respectively, and determine the type of the head movement according to a calculation result.

Specifically, the type determining unit 5212a may calculate cross correlations between the target waveform and the at least one reference waveform respectively to obtain calculation results corresponding to each reference waveform, and then may select the type corresponding to the reference waveform whose value of the calculation result is the highest (that is, reference waveform that has the highest degree of correlation with the target waveform) as the type of the head movement. For example, assume that the at least one reference waveform comprises a first reference waveform corresponding to head nodding and a second reference waveform corresponding to head shaking, a cross correlation between the first reference waveform and the target waveform is calculated to obtain a first result, and a cross correlation between the second reference waveform and the target waveform is calculated to obtain a second result, and if the value of the first result is higher than the value of the second result, it can be determined that the type of the head movement is head nodding.

Figure 8:
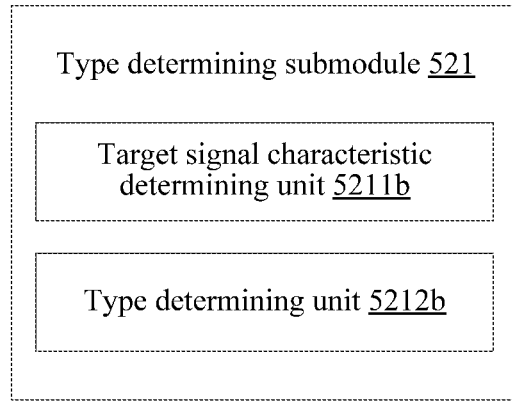
FIG. 8 is a module diagram of a type determining submodule according to another example embodiment of the present application.

In another example embodiment, referring to FIG. 8, the type determining submodule 521 may comprise:

a target signal characteristic determining unit 5211b, configured to determine a target signal characteristic in the piece of electrooculographic information; and a type determining unit 5212b, configured to determine the type of the head movement according to the target signal characteristic and at least one reference signal characteristic.

In the target signal characteristic determining unit 5211b, the target signal characteristic may be understood as a signal characteristic of the target waveform in the foregoing example embodiment, which is correlated with at least one of an amplitude, a phase, and a spectrum of the target waveform. Specifically, the target signal characteristic may comprise at least one of a fingerprint, an average value, and a difference; the fingerprint may be composed of at least one of the amplitude, phase, and spectrum of the target waveform; the average value may be an average value of at least one of the amplitude, phase, and spectrum of the target waveform; and the difference may be a difference of at least one of the amplitude, phase, and spectrum of the target waveform. Certainly, a person skilled in the art understands that the target signal characteristic may be directly determined according to data of the electrooculographic information, and does not have to be determined according to the target waveform.

In the type determining unit 5212b, the reference signal characteristic may be a signal characteristic that corresponds to a corresponding head movement obtained through pre-training, for example, during the training phase, the user may be trained to perform head movements of different types and the signal characteristics of the corresponding electrooculographic information are correspondingly acquired as the reference signal characteristics. For example, during the training phase, the user is trained to perform a head nodding movement, and a signal characteristic of the waveform in the ellipse in FIG. 2 is correspondingly acquired as a reference signal characteristic corresponding to the head nodding movement.

In the type determining unit 5212b, whether the target signal characteristic comprises the at least one reference signal characteristic may be determined in a signal characteristic comparison manner, and if yes, it is determined that the type of the head movement is a type corresponding to the comprised reference signal characteristic.

Figure 9:
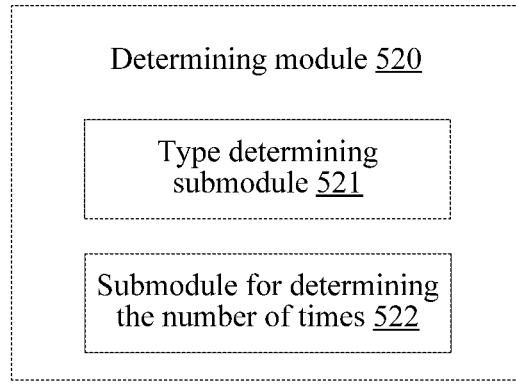
FIG. 9 is a module diagram of a determining module according to another example embodiment of the present application.

The type of the head movement may indicate different operating commands, for example, head nodding indicates confirmation and head shaking indicates cancelation. Meanwhile, for head movements of different types, different numbers of execution times may also indicate different operating commands, for example, a single head nodding indicates selected and two continuous head noddings indicate open. Therefore, in an example embodiment, the head movement comprises a first type head movement; and the at least one piece of reference information comprises first reference information corresponding to the first type head movement. Correspondingly, referring to FIG. 9, in another example embodiment, the determining module 520 further comprises:

a submodule for determining the number of times 522, configured to determine the number of times of the first type head movement according to the piece of electrooculographic information and the first reference information.

Figure 10:
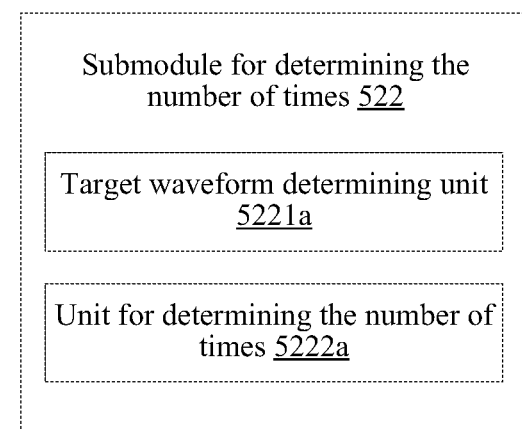
FIG. 10 is a module diagram of a submodule for determining the number of times according to an example embodiment of the present application.

In an example embodiment, referring to FIG. 10, the submodule for determining the number of times 522 may comprise:

a target waveform determining unit 5221a, configured to determine the target waveform in the piece of electrooculographic information; and a unit for determining the number of times 5222a, configured to determine the number of times of the first type head movement according to the number of first reference waveforms comprised in the target waveform.

A principle of the target waveform determining unit 5221a can be the same as the principle of the target waveform determining unit 5211a in the foregoing example embodiment, and no further details are provided herein again.

In the unit for determining the number of times 5222a, the number of the first reference waveforms comprised in the target waveform is corresponding to the number of times of the first type head movement. Assume that the first type head movement is head nodding, and the first reference waveform is a reference waveform corresponding to the head nodding. Taking FIG. 2 for example, it can be seen that the target waveform comprises two first reference waveforms, so that it can be determined that the user nods twice. Similarity, the electrooculographic information shown in FIG. 3 indicates that the user shakes the head twice.

Figure 11:
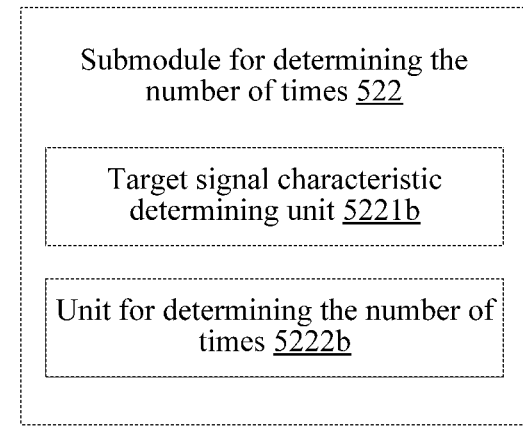
FIG. 11 is a module diagram of a submodule for determining the number of times according to another example embodiment of the present application.

In another example embodiment, referring to FIG. 11, the submodule for determining the number of times 522 comprises:

a target signal characteristic determining unit 5221b, configured to determine the target signal characteristic in the piece of electrooculographic information; and a unit for determining the number of times 5222b, configured to determine the number of times of the first type head movement according to the number of first reference signal characteristics comprised in the target signal characteristic.

A principle of the target signal characteristic determining unit 5221*b* can be the same as the principle of the target signal characteristic determining unit 5211*b* in the foregoing example embodiment, and no further details are provided herein again.

In the unit for determining the number of times 5222*b*, the target signal characteristic comprises the number of the first reference signal characteristics, which is corresponding to the number of times of the first type head movement. Still assume that the first type head movement is head nodding, and assume that the first reference signal characteristic is amplitude changing data (for example, the amplitude is decreased to smaller than −20 first, and then increased to greater than 20, and decreased to smaller than −20 again) corresponding to the head nodding. Taking FIG. 2 for example, it can be seen that the target signal characteristic in the electrooculographic information comprises two first reference signal characteristics, so that it can be determined that the user nods twice. Certainly, a person skilled in the art understands that in the step, the waveform curve shown in FIG. 2 does not have to be obtained. Similarity, the electrooculographic information shown in FIG. 3 indicates that the user shakes the head twice.

In addition, the head movement may further comprise head movements of other types, for example, a second type head movement, or the head movement may comprise head movements of multiple types simultaneously, for example, the head movement may comprise the first type head movement and the second type head movement simultaneously, and identification of the number of times of the head movements of various types may be implemented according to the foregoing principle.

Figure 12:
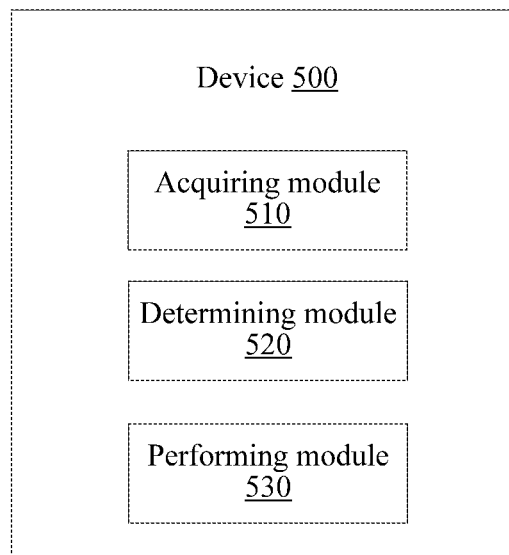
FIG. 12 is a module diagram of a device for determining a head movement according to another example embodiment of the present application.

Referring to FIG. 12, in an example embodiment, the device 500 further comprises:

a performing module 530, configured to perform an operation according to a determination result.

The performed operation may comprise operations such as mode switching, content entering, user reminding, and device matching.

In summary, in the device of an embodiment of the present application, a head movement of a user may be determined according to electrooculographic information, and a corresponding operation is performed, which facilitates the user to control a corresponding electronic device by a head movement without adding implementation costs.

An application scenario of determining a head movement of embodiments of the present application may as follows: a user wears a pair of glasses, and the pair of glasses initially enters a first level menu, an electrooculographic sensor thereon acquires an electrooculographic signal of the user; the user performs a head shaking movement, and the pair of glasses identifies the head shaking movement, and therefore controls items of the first level menu to switch in a display window of the pair of glasses according to a predefined sequence; and when an application a user wants to open is switched to, the user performs a head nodding movement, the application is selected, and then the user nods twice continuously, the application is open.

Figure 13:
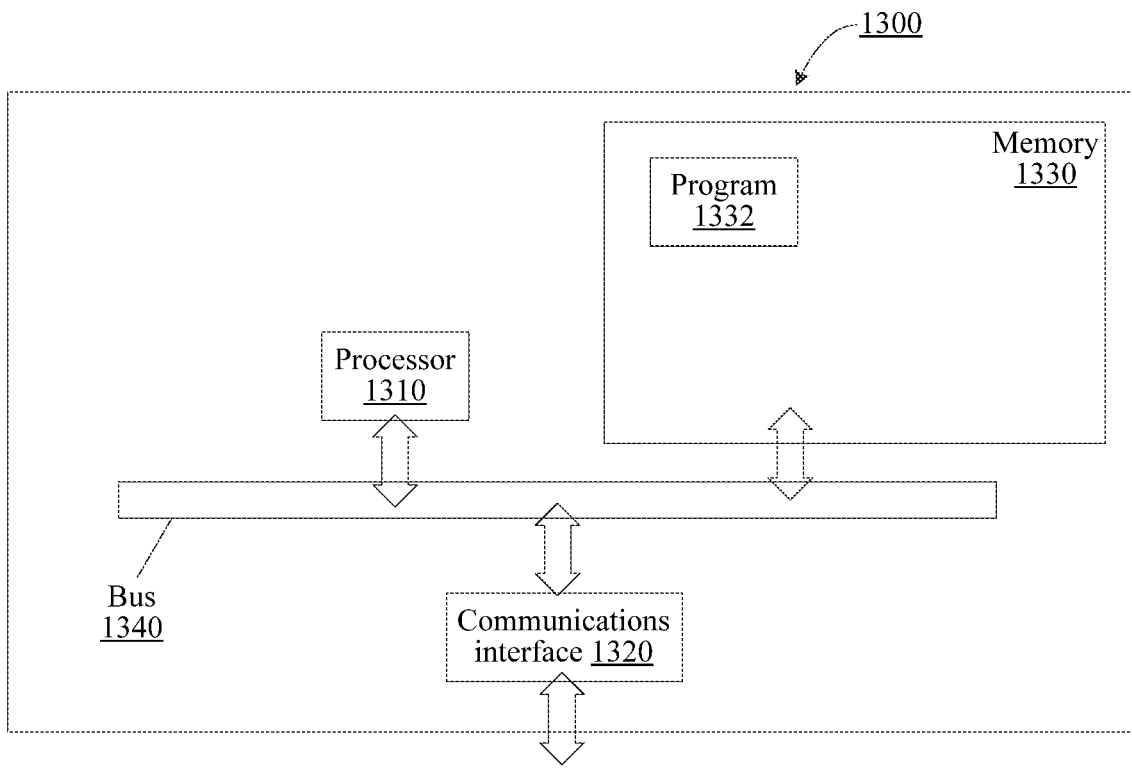
FIG. 13 is a schematic hardware structural diagram of a device for determining a head movement according to an example embodiment of the present application.

A hardware structure of a device for determining a head movement according to another embodiment of the present application is shown in FIG. 13. Specific embodiments of the present application are not intended to limit embodiments of the device for determining a head movement. As shown in FIG. 13, the device 1300 may comprise:

a processor 1310, a communications interface 1320, a memory 1330, and a communications bus 1340.

The processor 1310, the communications interface 1320, and the memory 1330 communicate with each other by using the communications bus 1340.

The communications interface 1320 is configured to communicate with other network elements.

The processor 1310 is configured to execute a program 1332. Specifically, the processor 1310 may perform relevant steps in the foregoing method embodiment shown in FIG. 1.

Specifically, the program 1332 may comprise program code, wherein the program code comprises a computer operation instruction.

The processor 1310 may be a central processing unit (CPU), an application specific integrated circuit (ASIC), or one or more integrated circuits configured to implement embodiments of the present application.

The memory 1330 is configured to store the program 1332. The memory 1330 may comprise a high-speed RAM memory, or may further comprise a non-volatile memory, for example, at least one magnetic disk storage. The program 1332 may be specifically used to perform the following steps:

acquire, in response to a head movement performed by a user, a piece of electrooculographic information of the user; and determine information related to the head movement according to the piece of electrooculographic information and at least one piece of reference information.

For the steps in the program 1332, reference may be made to the corresponding steps or modules in the foregoing embodiments, and no further details are provided herein again. It may be clearly understood by a person skilled in the art that, for the purpose of convenient and brief description, for detailed working procedures of the foregoing devices and modules, reference may be made to the description of corresponding procedures in the foregoing method embodiments, and no further details are provided herein again.

A person of ordinary skill in the art may be aware that, in combination with the examples described in embodiments disclosed in this specification, units and method steps may be implemented by means of electronic hardware or a combination of computer software and electronic hardware. Whether these functions are executed as hardware or software depends upon the particular application and design constraint conditions of the technical solutions. A person skilled in the art may use different methods to implement the described functions for each particular application, but it should not be considered that the embodiment goes beyond the scope of the present application.

When the functions are implemented in a form of a software functional unit and sold or used as an independent product, the functions may be stored in a computer-readable storage medium. Based on such an understanding, the technical solutions of the present application essentially, or the part contributing to the prior art, or some of the technical solutions may be implemented in a form of a software product. The computer software product is stored in a storage medium, and comprises several instructions for instructing a computer device (which may be a personal computer, a server, a network device, or the like) to perform all or some of the steps of the methods in embodiments of the present application. The foregoing storage medium comprises: any medium that can store program code, such as a USB flash drive, a removable hard disk, a read-only memory (ROM), a random access memory (RAM), a magnetic disk, or an optical disc.

The above example embodiments are only used to describe the present application, rather than limit the present application; various alterations and variants can be made by a person of ordinary skill in the art without departing from the spirit and scope of the present application, so all equivalent technical solutions also belong to the scope of the present application, and the scope of patent protection of the present application should be defined by claims.

What is claimed is:

1. A method for determining a head movement, comprising:
   acquiring, by a system comprising a processor, in response to a head movement performed by a user, a piece of electrooculographic information of the user; and
   determining, by the system, movement information related to the head movement according to the piece of electrooculographic information and at least one piece of reference information, wherein the movement information comprises a type of the head movement, and the determining comprises:
      determining a target waveform from the piece of electrooculographic information, and
      determining the type of the head movement according to the target waveform and at least one reference waveform, wherein the reference waveform is a waveform that corresponds to a corresponding head movement obtained through pre-training during a training phase.

2. The method according to claim 1, wherein the type of the head movement comprises: at least one of a nodding type representative of a head nodding and a shaking type representative of a head shaking.

3. The method according to claim 1, wherein the determining the type of the head movement according to the target waveform and the at least one reference waveform comprises:
   determining the type of the head movement according to a calculation result based on cross correlations determined between the target waveform and the at least one reference waveform respectively.

4. The method according to claim 1, wherein the determining the type of the head movement further comprises:
   determining a target signal characteristic from the piece of electrooculographic information; and
   determining the type of the head movement according to the target signal characteristic and at least one reference signal characteristic.

5. The method according to claim 1, wherein the type of the head movement comprises a first type of head movement,
   the at least one piece of reference information comprises first reference information corresponding to the first type of head movement, and
   the determining the movement information related to the head movement according to the piece of electrooculographic information and the at least one piece of reference information further comprises:
   determining a number of times of movement according to the first type of head movement according to the piece of electrooculographic information and the first reference information.

6. The method according to claim 5, wherein the determining the number of times of movement of the first type of head movement according to the piece of electrooculographic information and the first reference information comprises:
   determining a target signal characteristic in the piece of electrooculographic information; and
   determining the number of times of movement of the first type of head movement according to a number of first reference signal characteristics comprised in the target signal characteristic.

7. The method according to claim 1,
   determining a number of times of movement of the type of the head movement according to a number of the reference waveform comprised in the target waveform.

8. The method according to claim 1, further comprising:
   performing, by the system, an operation according to a determination result of the determining the movement information.

9. A device, comprising:
   a memory that stores executable modules; and
   a processor, coupled to the memory, that executes or facilitates execution of the executable modules, the executable modules comprising:
      an acquiring module configured to acquire, in response to a head movement of a user, a piece of electrooculographic information of the user; and
      a determining module configured to determine head movement information related to the head movement at least according to the piece of electrooculographic information and at least one piece of reference information, wherein the movement information comprises a type of the head movement, and the determination of the type of the head movement comprises:
         determine a target waveform from the piece of electrooculographic information, and
         determine the type of the head movement according to the target waveform and at least one reference waveform, wherein the reference waveform is a waveform that corresponds to a corresponding head movement obtained through pre-training during a training phase.

10. The device according to claim 9, wherein the determination of the type of the head movement is based on a result of calculating cross correlations between the target waveform and the at least one reference waveform respectively.

11. The device according to claim 9, wherein the determination of the type of the head movement further comprises:
   determine a target signal characteristic represented in the piece of electrooculographic information; and
   determine the type of the head movement according to the target signal characteristic and at least one reference signal characteristic.

12. The device according to claim 9, wherein the type of the head movement comprises a first type of head movement,
   the at least one piece of reference information comprises first reference information corresponding to the first type head movement, and
   the determining module is further configured to determine a number of times of the first type of head movement according to the piece of electrooculographic information and the first reference information.

13. The device according to claim 12, wherein the determining module is further configured to:
   determine a target signal characteristic represented in the piece of electrooculographic information; and determine the number of times of the first type head movement according to a number of first reference signal characteristics comprised in the target signal characteristic.

14. The device according to claim 9, wherein the determining module is further configured to determine a number of times of the type of the head movement according to a number of the reference waveform comprised in the target waveform.

15. The device according to claim 9, wherein the executable modules further comprise:
a performing module configured to perform an operation according to a determination result of the determining module.

16. The device according to claim 9, wherein the device is included in a wearable device.

17. A wearable device for determining a head movement, comprising at least one executable instruction, which, in response to execution, causes the wearable device comprising a processor to perform operations, comprising:
in response to a head movement determined to be associated with a user identity, acquiring a piece of electrooculographic information of the user identity; and
determining movement information related to the head movement based at least in part on the piece of electrooculographic information and a piece of reference information, wherein the movement information comprises a type of the head movement, and the determining comprises:
determining a target waveform from the piece of electrooculographic information, and
determining the type of the head movement according to the target waveform and at least one reference waveform, wherein the reference waveform is a waveform that corresponds to a corresponding head movement obtained through pre-training during a training phase.

18. A non-transitory computer-readable medium having instructions stored thereon that, in response to execution, cause a system including a processor to perform operations, comprising:
acquiring, in response to a head movement performed by a user, at least one piece of electrooculographic information of the user; and
determining movement information related to the head movement at least according to the at least one piece of electrooculographic information and at least one piece of reference information, wherein the movement information comprises a type of the head movement, and the determining comprises:
determining a target waveform from the piece of electrooculographic information, and
determining the type of the head movement according to the target waveform and at least one reference waveform, wherein the reference waveform is a waveform that corresponds to a corresponding head movement obtained through pre-training during a training phase.

19. The non-transitory computer-readable medium of claim 18, wherein the type of the head movement comprises: at least one of a nodding type representative of a head nodding and a shaking type representative of a head shaking.

20. The non-transitory computer-readable medium of claim 18, wherein the determining the type of the head movement according to the target waveform and the at least one reference waveform comprises:
determining the type of the head movement according to a calculation result based on cross correlations determined between the target waveform and the at least one reference waveform respectively.

21. The non-transitory computer-readable medium of claim 18, wherein the determining the type of the head movement further comprises:
determining a target signal characteristic from the piece of electrooculographic information; and
determining the type of the head movement according to the target signal characteristic and at least one reference signal characteristic.

22. The non-transitory computer-readable medium of claim 18, wherein the operations further comprise:
determining a number of times of movement of the type of the head movement according to a number of the reference waveform comprised in the target waveform.

* * * * *